US009527785B2

(12) United States Patent
Blackmon et al.

(10) Patent No.: US 9,527,785 B2
(45) Date of Patent: Dec. 27, 2016

(54) METHOD OF FORMING C5 DI-OLEFINS

(71) Applicant: FINA TECHNOLOGY, INC., Houston, TX (US)

(72) Inventors: Kenneth Paul Blackmon, Houston, TX (US); Sivadinarayana Chinta, Missouri City, TX (US); Jun Wang, Houston, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 102 days.

(21) Appl. No.: 14/204,527

(22) Filed: Mar. 11, 2014

(65) Prior Publication Data

US 2014/0288343 A1 Sep. 25, 2014

Related U.S. Application Data

(60) Provisional application No. 61/803,256, filed on Mar. 19, 2013.

(51) Int. Cl.
*C07C 2/86* (2006.01)

(52) U.S. Cl.
CPC ........... *C07C 2/867* (2013.01); *C07C 2521/12* (2013.01); *C07C 2521/16* (2013.01); *C07C 2529/08* (2013.01); *C07C 2529/40* (2013.01); *C07C 2529/44* (2013.01); *C07C 2529/83* (2013.01)

(58) Field of Classification Search
None
See application file for complete search history.

(56) References Cited

U.S. PATENT DOCUMENTS

| 2,335,691 | A | * | 11/1943 | Mottern | C07C 2/867 585/608 |
|---|---|---|---|---|---|
| 3,004,084 | A | | 10/1961 | Oldham | |
| 3,146,278 | A | | 8/1964 | Habeshaw et al. | |
| 3,414,588 | A | | 12/1968 | Jones | |
| 3,501,550 | A | | 3/1970 | Brandt et al. | |
| 4,002,578 | A | * | 1/1977 | Csicsery | B01J 29/084 502/64 |
| 4,092,372 | A | | 5/1978 | Furuoya et al. | |
| 4,252,632 | A | * | 2/1981 | Mooi | B01J 23/56 208/113 |
| 4,293,449 | A | * | 10/1981 | Herrington | B01J 37/024 423/628 |
| 4,608,355 | A | * | 8/1986 | Chu | B01J 29/064 502/68 |
| 2004/0138051 | A1 | * | 7/2004 | Shan | B01J 21/06 502/60 |

(Continued)

FOREIGN PATENT DOCUMENTS

| WO | 9601687 A1 | 1/1996 |
| WO | 2011085223 A1 | 7/2011 |

OTHER PUBLICATIONS

International Search Report and Written Opinion issued in PCT Patent Application No. PCT/US14/23558, dated Jun. 20, 2014 (11 pages).

(Continued)

*Primary Examiner* — In Suk Bullock
*Assistant Examiner* — Alyssa L Cepluch
(74) *Attorney, Agent, or Firm* — Albert Shung

(57) ABSTRACT

A process is disclosed that includes reacting a C1 source with n-butene to form a C-5 diolefin.

15 Claims, 3 Drawing Sheets

(56) References Cited

U.S. PATENT DOCUMENTS

2012/0296140 A1* 11/2012 Chinta .................... C07C 2/862
   585/437

OTHER PUBLICATIONS

J. Haber, et al., "Manual of Methods and Procedures for Catalyst Characterization (Technical Report)", International Union of Pure and Applied Chemistry, vol. 67, Nos. 8/9, pp. 1257-1306, 1995.
Ivanova I., et al., "Synthesis of isoprene from formaldehyde and isobutene over phosphate catalysts" Appl Cat A, 2012, 441-442, pp. 21-29.
Office Action for Chinese Application No. 201480016373.6, dated Aug. 11, 2016, 14 pages.
"Gas-phase condensation reaction of olefins with formaldehyde by silica-alumina catalyst", Dec. 31, 1968; 22 pages.

* cited by examiner

METHOD OF FORMING C5 DI-OLEFINS

CROSS-REFERENCE TO RELATED APPLICATIONS

This application is a Non-Provisional of U.S. Provisional Application No. 61/803,256, filed on Mar. 19, 2013.

FIELD

The present disclosure relates to a method for the production of C5 Di-olefins. More specifically, the disclosure relates to the alkylation of butene with a carbon source (herein referred to as a C-1 source) to produce a product stream that includes piperylene (1,3-pentadiene) and/or isoprene (2 methyl-1,3-butadiene).

BACKGROUND

Piperylene may be used as an intermediate monomer in the manufacture of plastics, adhesives and resins. Piperylene-based products are often used in modern adhesives, such as those used in the manufacture of envelopes, parcel tapes and diaper fastenings, and in road markings. Piperylene has been traditionally produced as part of the preparation of crude C5 material from pygas. It may be derived from crude oil via a number of extraction steps.

High-purity isoprene is used as a monomer in the production of polyisoprene rubber (IR), styrenic thermoplastic elastomer block copolymers (styrene-isoprene-styrene [SIS]) and butyl rubber. Isoprene may also be converted into specialty chemicals, including vitamins, pharmaceuticals, flavorings and perfumes, and epoxy hardeners. Isoprene has traditionally been produced as a byproduct of the thermal cracking of naphtha or oil, as a side product in the production of ethylene.

SUMMARY

A process is disclosed that includes reacting a C1 source with n-butene to form a C-5 diolefin.

DETAILED DESCRIPTION

In an embodiment of the present disclosure, n-butene (1-butene or 2-butene) is reacted with a carbon source (hereinafter a "C-1 source") capable of coupling with n-butene to form a product stream containing C5 Di-olefins. In certain embodiments, the C-1 source includes methanol or formaldehyde or a mixture of the two. In a further embodiment, the C-1 source may be methanol, formaldehyde, formalin (37-50% $H_2CO$ in solution of water and MeOH), trioxane (1,3,5-trioxane), methylformcel (55% $H_2CO$ in methanol), paraformaldehyde and methylal (dimethoxymethane), and combinations thereof. In certain non-limiting embodiments, formaldehyde may be produced by the partial oxidation or dehydrogenation of methanol and partial oxidation of methane.

Formation of Formaldehyde

In an embodiment, formaldehyde may be manufactured by the dehydrogenation of methanol to produce formaldehyde and hydrogen gas. In this reaction, a dry formaldehyde stream may be produced. The dehydrogenation process may be described by:

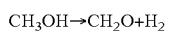

$$CH_3OH \rightarrow CH_2O + H_2$$

In another embodiment, formaldehyde may be produced by the oxidation of methanol. The oxidation of methanol may be described by:

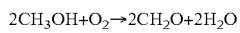

$$2CH_3OH + O_2 \rightarrow 2CH_2O + 2H_2O$$

A separation unit may then be used to separate the hydrogen gas or water from the formaldehyde and unreacted methanol prior to reacting the formaldehyde with n-butene for the production of piperylene.

Formation of Piperylene

In one embodiment of the present disclosure, the process of forming piperylene may be represented by:

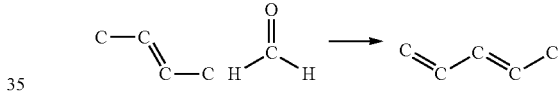

Stoichiometrically, the reaction of n-butene with formaldehyde is 1:1 molar ratio. However, the feed ratio may vary in certain embodiments of the present disclosure and may vary depending on conditions including, but not limited to operating conditions and the efficiency of the reaction system. In certain embodiments, the ratio of n-butene:formaldehyde may range from between 100:1 to 1:100. In alternate embodiments the ratio of n-butene:formaldehyde source may range between from 50:1 to 1:50; from 20:1 to 1:20; from 10:1 to 1:10; or from 5:1 to 1:5.

Figure 1:
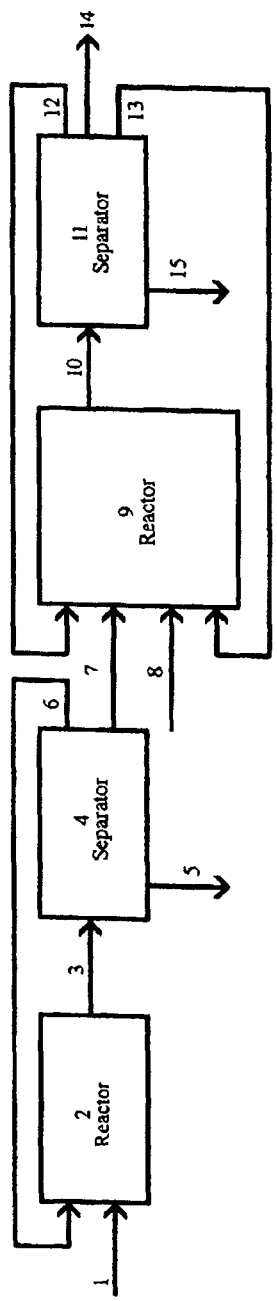
FIG. 1 illustrates a flow chart for the production of C5 Di-olefins by the reaction of formaldehyde and n-butene, wherein the formaldehyde is first produced in a separate reactor by either the dehydrogenation or oxidation of methanol and is then reacted with n-butene to produce C5 Di-olefins.

FIG. 1 depicts a simplified flow chart of one non-limiting embodiment of the C5 Di-olefins production process described above. In this embodiment, first reactor (2) is a dehydrogenation reactor or an oxidation reactor. This reactor is designed to convert first methanol feed (1) into formaldehyde. Product stream (3) of first reactor (2) may be processed in separation unit (4) where the formaldehyde is separated from unreacted methanol (6) and byproducts (5). Unreacted methanol (6) may be recycled to first reactor (2). Byproducts (5) may be separated from formaldehyde (7).

In one embodiment, first reactor (2) is a dehydrogenation reactor that produces formaldehyde and hydrogen and separation unit (4) may be a membrane capable of removing hydrogen from product stream (3).

In an alternate embodiment, first reactor (2) is an oxidative reactor and product stream (3) may include formaldehyde and water. Product stream (3) may be sent to the second reactor (9) without separation unit (4).

Formaldehyde (7), or alternatively, product stream (3) (not shown) may be reacted with n-butene stream (8) in second reactor (9). The n-butene and formaldehyde react to produce second reactor product stream (10), which may include 2-methyl butene-1, N-pentane, iso-pentane, t-2 pentene, c-2 pentene, 2-methyl butene, t-1,3 pentadiene and c-1,3-pentadiene. In certain embodiments of the present disclosure, 1,3 pentadiene is the primary product. Second reactor product stream (10) may be processed in separation unit (11) where any second reactor byproducts (15), such as water, may be separated from second reactor product stream (10). Unreacted formaldehyde (12) and unreacted n-butene (13) may also be separated from second reactor product stream (10) and be recycled to second reactor (9). Final product stream (14) may be removed from the separation unit (11) and subjected to further treatment or processing if desired.

The operating conditions of the reactors and separators may vary depending on the feedstream composition and the desired composition of the product streams. Second reactor (9) may operate at elevated temperatures and pressures and may contain a basic or acidic/neutral catalyst system. Temperature in second reactor (9) may range in non-limiting examples from 200° C. to 750° C., 300° C. to 500° C., or 225° C. to 450° C. The pressure in second reactor (9) may range in non-limiting examples from 1 atm to 150 atm, from 1 atm to 35 atm, or from 1 atm to 5 atm.

Figure 2:
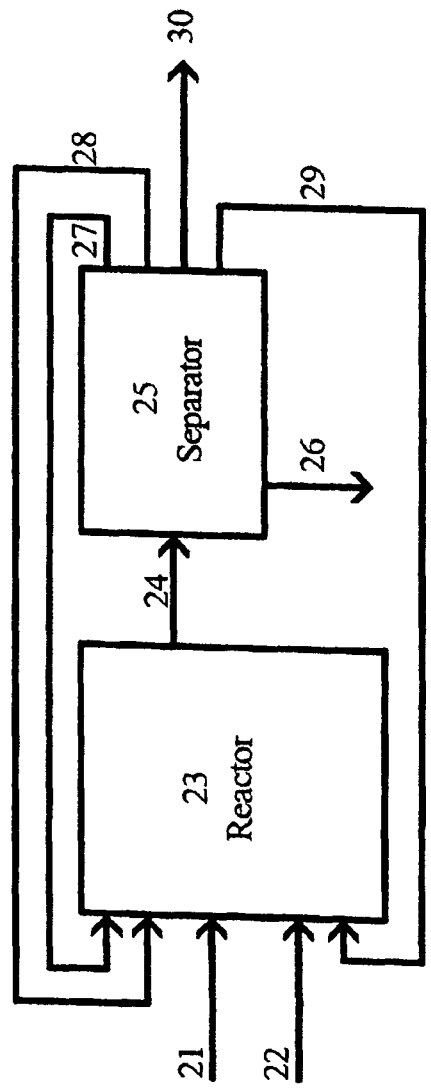
FIG. 2 illustrates a flow chart for the production of C5 Di-olefins by the reaction of formaldehyde and C5 Di-olefins, wherein methanol and C5 Di-olefins are fed into a reactor, wherein the methanol is converted to formaldehyde and the formaldehyde is reacted with n-butene to produce C5 Di-olefins.

FIG. 2 depicts a simplified flow chart of a second non-limiting embodiment of the C5 Di-olefins production process described above. C-1 source-containing feed stream (21) is fed with n-butene stream (22) to primary reactor (23). n-butene and the C-1 source react in primary reactor (23) to produce product stream (24). Product stream (24) of primary reactor (23) may be sent to separation unit (25) where byproducts (26) may be separated from product stream (24), and any unreacted C-1 source (27), unreacted methanol (29), unreacted formaldehyde and unreacted n-butene (28) may be may be recycled to primary reactor (23). Final product stream (30) may be removed from separation unit (25) and subjected to further treatment or processing if desired.

The operating conditions of the reactors and separators may vary depending on conditions such as feedstream composition and the desired composition of the product streams. Primary reactor (23) may operate at elevated temperatures and pressures and may contain a basic or acidic/neutral catalyst system. The temperature may range in non-limiting examples from 200° C. to 750° C., 300° C. to 500° C., or 225° C. to 450° C. The pressure may range in non-limiting examples from 1 atm to 150 atm, 1 atm to 35 atm, or 1 atm to 5 atm.

Catalyst Systems—Zeolites

Basic or Neutral Zeolites

The catalytic reaction systems suitable for this disclosure may include basic or neutral zeolites comprising silica, alumina or combination of, silicate-based zeolites, for instance faujasites, mordenites, etc. Silicate-based zeolites are made of alternating $SiO_2$ and $MO_x$ tetrahedra, where M is an element selected from the Groups 1 through 16 of the Periodic Table (new IUPAC). These types of zeolites have 4-, 6-, 8-, 10-, or 12-membered oxygen ring channels.

Non-limiting examples may include zeolites promoted with one or more of the following: Fe, Co, Mo, Ag, Bi, W, Ru, Rh, Ni, Co, Pd, Pt, Mn, Ti, Zr, V, Nb, K, Cs, Ga, B, P or Na. In an embodiment, the zeolite may be promoted with one or more of Cs, B, Co, Fe, Mo, Ag, Bi, W or Ga. In general, the promoter exchanges with Na within the zeolite or amorphous material. Promoter may also be attached to the zeolite or amorphous material in an occluded manner.

The zeolite catalyst is adaptable to use in the various physical forms in which catalysts are commonly used. The catalyst of the disclosure may be used as a particulate material in a contact bed or as a coating material on structures having a high surface area. If desired, the catalyst may be deposited with various catalyst binder and/or support materials.

A zeolite catalyst comprising a substrate that supports a promoting metal or a combination of metals may be used to catalyze the reaction of hydrocarbons. The method of preparing the catalyst, pretreatment of the catalyst, and reaction conditions may influence the conversion, selectivity, and yield of the reactions.

The various elements that make up the catalyst may be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds may be prepared by any suitable method, known in the art, for the preparation of such materials.

The term "substrate" as used herein is not meant to indicate that this component is necessarily inactive, while the other metals and/or promoters are the active species. The substrate may be an active part of the catalyst. The term "substrate" would merely imply that the substrate makes up a significant quantity, generally 10% or more by weight, of the entire catalyst. The promoters individually may range from 0.01% to 60% by weight of the catalyst, optionally from 0.01% to 50%. If more than one promoters are combined, they together generally may range from 0.01% up to 70% by weight of the catalyst. The elements of the catalyst composition may be provided from any suitable source, such as in its elemental form, as a salt, as a coordination compound, etc.

In certain embodiments, the addition of a support material may be added to improve the catalyst physical properties. Binder material, extrusion aids or other additives may be added to the catalyst composition or the final catalyst composition may be added to a structured material that provides a support structure. For example, the final catalyst composition may include an alumina or aluminate framework as a support. Upon calcination these elements may be altered, such as through oxidation, which may increase the relative content of oxygen within the final catalyst structure. The combination of the catalyst of the present disclosure combined with additional elements such as a binder, extrusion aid, structured material, or other additives, and their respective calcination products, are included within the scope of the disclosure.

In one embodiment, the zeolite catalyst may be prepared by combining a substrate with at least one promoter element. Embodiments of a substrate may be a molecular sieve, from either natural or synthetic sources. Zeolites and zeolite-like materials may be an effective substrate. Alternate molecular sieves also contemplated are zeolite-like materials such as the crystalline silicoaluminophosphates (SAPO) and the aluminophosphates (ALPO).

The present disclosure is not limited by the method of catalyst preparation, and all suitable methods should be considered to fall within the scope herein. Particularly effective techniques are those utilized for the preparation of solid catalysts. Conventional methods include co-precipitation from an aqueous, an organic or a combination solution-dispersion, impregnation, dry mixing, wet mixing or the like, alone or in various combinations. In general, any method may be used which provides compositions of matter containing the prescribed components in effective amounts. According to an embodiment, the substrate is charged with promoter via an incipient wetness impregnation. Other impregnation techniques such as by soaking, pore volume impregnation, or percolation may optionally be used. Alternate methods such as ion exchange, wash coat, precipitation, and gel formation may also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

When slurries, precipitates or the like are prepared, they may be dried, usually at a temperature sufficient to volatilize the water or other carrier, such as from 100° C. to 250° C., with or without vacuum. Irrespective of how the components are combined and irrespective of the source of the components, the dried composition may be calcined in the presence of a free oxygen-containing gas, usually at temperatures between about 300° C. and about 900° C. for from 1 to 24 hours. The calcination may be in an oxygen-containing atmosphere, or alternately in a reducing or inert atmosphere.

The prepared catalyst may be ground, pressed, sieved, shaped and/or otherwise processed into a form suitable for loading into a reactor.

Basic or Neutral Zeolites with Occluded Metal Oxides

Other embodiments of the present disclosure are directed to a metal ion modified species of a catalyst, such as a zeolite catalyst, to enhance conversion and product selectivity in an alkylation reaction. Specifically, a zeolite may be modified by the addition of an occluded metal oxide, such as cesium oxide, copper oxide, or cerium oxide, in a way that results in improved conversion and product selectivity and inhibits unwanted by-product formation of an alkylation reaction. As used herein, the term "metal ion" is meant to include all active metal ions and similar species, such as metal oxides, and mixed metal oxide phases. Further, the term "ion-modified zeolite" as used herein refers to a zeolite that has been modified with a metal ion to enhance product selectivity.

The ion-modified zeolites may include metal oxide species, such as for a non-limiting example cesium oxide species like $Cs_2O$. The metal oxide may be present within the structure of the zeolite, or support. The metal oxide present within the structure of the zeolite may be loosely contained within the structure of the zeolite. In an embodiment the metal oxide is not attached to the zeolite, but physically trapped within the zeolite cage structure, which may be referred to herein as occluded metal oxide or occluded cesium. In an embodiment, occluded cesium oxide present in the structure of the zeolite may electrically influence the zeolite and alter its catalytic abilities.

In an embodiment, occluded metal oxide species may be present in an amount of from 0.1 to 10 metal oxide species per unit cell of the zeolite or zeolite like material. Optionally the occluded metal oxide species may be present in an amount of from 1 to 7 metal oxide species per unit cell, optionally from 2 to 4 metal oxide species per unit cell.

In an embodiment, occluded cesium oxide species may be present in an amount of from 0.1 to 10 Cs per unit cell of the zeolite or zeolite like material. Optionally the occluded cesium oxide may be present in an amount of from 1 to 7 Cs per unit cell, optionally from 2 to 4 Cs per unit cell.

In an embodiment, occluded copper oxide species may be present in an amount of from 0.1 to 10 Cu per unit cell of the zeolite or zeolite like material. Optionally the occluded copper oxide may be present in an amount of from 1 to 7 Cu per unit cell, optionally from 2 to 4 Cu per unit cell.

In an embodiment, occluded cerium oxide species may be present in an amount of from 0.1 to 10 Ce per unit cell of the zeolite or zeolite like material. Optionally the occluded cerium oxide may be present in an amount of from 1 to 7 Ce per unit cell, optionally from 2 to 4 Ce per unit cell.

In an embodiment, the catalyst having occluded metal oxide in the support may further have additional metal ions added as a promoter on the support through a method such as ion exchange. The metal ions added through ion exchange are added by replacement of a cation of the support lattice, such as sodium or potassium, with the metal ion. In an embodiment the additional metal ions may range from 0.1 to 80% of the cations of the zeolite, optionally from 10 to 60% of the cations of the zeolite, optionally from 25 to 40% of the cations of the zeolite.

In an embodiment, the catalyst having occluded cesium oxide in the support may further have additional cesium ions added as a promoter on the support through a method such as ion exchange. The cesium ions added through ion exchange are added by replacement of a cation of the support lattice, such as sodium or potassium. In an embodiment the additional cesium ions may range from 0.1 to 80% of the cations of the zeolite, optionally from 10 to 60% of the cations of the zeolite, optionally from 25 to 40% of the cations of the zeolite. In a like manner copper or cerium may be used as an occluded metal oxide and may have additional promoters added through ion exchange.

The ion-modified catalyst of the present disclosure having occluded metal oxide in the support may increase the n-butene conversion. However, the presence of the metal oxide may decrease the utilization of the C-1 source. The C-1 utilization may be increased by the addition of promoters. In an embodiment, the C-1 utilization may be enhanced by the addition of boron (B) has a promoter. In an embodiment the boron in the catalyst may range from 0.01 wt % to 5 wt %, optionally from 0.1 wt % to 2 wt %, optionally from 0.4 wt % to 0.8 wt %.

In an embodiment, the metal ion may be added to the zeolite in the amount of 0.1% to 50%, optionally 0.1% to 20%, optionally 0.1% to 5%, by weight of the zeolite. The metal ion may be added to the zeolite by any means known in the art. Generally, the method used is incipient wetness impregnation, wherein the metal ion precursor is added to an aqueous solution, which solution is poured over the zeolite. After sitting for a specified period, the zeolite may be dried and calcined, such that the water is removed with the metal ion deposited on the zeolite surface. In an embodiment, the ion-modified zeolite may then be mixed with a binder by any means known in the art. The zeolite, or zeolite binder mixture, is shaped via extrusion or some other method into a form such as a pellet, tablet, cylinder, cloverleaf, dumbbell, symmetrical and asymmetrical polylobates, sphere, or any other shape suitable for the reaction bed. The shaped form is then usually dried and calcined. Drying may take place at a temperature of from 100° C. to 200° C. Calcining may take place at a temperature of from 400° C. to 900° C. in a substantially dry environment. The resultant catalyst aggregate may contain binder in concentrations of from 1% to 80%, optionally from 5% to 50%, optionally from 10% to 30%, by weight.

The powder form of zeolite and other catalysts may be unsuitable for use in the reactor, due to a lack of mechanical stability, making alkylation and other desired reactions difficult. To render a catalyst suitable for the reactor, it may be combined with a binder to form an aggregate, such as a zeolite aggregate, with enhanced mechanical stability and strength. The aggregate may then be shaped or extruded into a form suitable for the reaction bed. The binder may desirably withstand temperature and mechanical stress and ideally does not interfere with the reactants adsorbing to the catalyst. It is possible for the binder to form macropores, much greater in size than the pores of the catalyst, which provide improved diffusional access of the reactants to the catalyst.

Binder materials that are suitable for the ion-modified zeolite of the present disclosure include, but are not limited to, silica, alumina, titania, zirconia, zinc oxide, magnesia, boria, silica-alumina, silica-magnesia, chromia-alumina, alumina-boria, silica-zirconia, silica gel, clays, similar species, and any combinations thereof. In certain embodiments, the binders are amorphous silica and alumina, including gamma-, beta-, and theta-alumina. A binder may be used with many different catalysts, including various forms of zeolite and non-zeolite catalysts that require mechanical support.

Basic or Neutral Zeolitic Nano-materials

Zeolites may tend to possess either only micropores or only mesopores, in most cases only micropores. Micropores are defined as pores having a diameter of less than about 2 μm. Mesopores are defined as pores having a diameter ranging from about 2 μm to about 50 μm. Micropores generally limit external molecules access to the catalytically active sites inside of the micropores or slow down diffusion to the catalytically active sites.

Embodiments of the present disclosure may utilize a nanosize zeolite. As used herein, the term "nanosize zeolite" refers to zeolitic materials having a particle size smaller than 1000 nm (1 μm). For example, the particle size may be less than 1000 nm, or less than 300 nm, or less than 100 nm, or less than 50 nm, or less than 25 nm, for example. In one or more embodiments, the particle size is from 1.0 nm to 1000 nm, or from 10 nm to 500 nm, or from 25 nm to 300 nm, or from 50 nm to 100 nm or from 50 nm to 75 nm, for example. As used herein, the "particle size" refers to either the size of each discrete crystal (i.e., crystal) of the zeolitic material or the size of an agglomeration of particles (i.e., crystallite) within the zeolitic material. The particles of nanosize zeolite may also be referred to as nanoparticles.

The nanosize zeolitic materials may include silicate-based zeolites, such as faujasites and mordenites, for example. Silicate-based zeolites may be formed of alternating $SiO_2$ and $MO_x$ tetrahedra, where M is an element selected from the Groups 1 through 16 of the Periodic Table. Such formed zeolites may have 4, 6, 8, 10, or 12-membered oxygen ring channels, for example. Examples of faujasites are X-type and Y-type zeolites. The nanosize zeolitic material may have a Si/Al ratio of 1.0 or greater. In an embodiment the Si/Al ratio may range from 1.0 to 200. In an alternate embodiment the Si/Al ratio may range from 1.0 to 100. In an alternate embodiment the Si/Al ratio may range from 1.0 to 50. In an alternate embodiment the Si/Al ratio may range from 1.0 to 25.

Optional support materials may include silica, alumina, aluminosilica, titania, zirconia and combinations thereof, for example. An optional support material may be a larger crystal size faujasite, such as a conventional sized zeolite, that may support a nanosize zeolite.

The catalyst generally includes from 1 wt. % to 99 wt. %, or from 3 wt. % to 90 wt. % or from 4 wt. % to 80 wt. % nanosize zeolite in the final catalyst, for example. In an embodiment the nanosize zeolite ranges from 5 wt. % to 50 wt. %, optionally from 5 wt. % to 30 wt. %. In one or more embodiments, the catalyst includes from 5 wt. % to 20 wt. %, or from 5 wt. % to 15 wt. % or from 7 wt. % to 12 wt. % support material in the final catalyst, for example.

In one or more embodiments, the nanosize zeolite may have an increased ratio of surface area to volume compared to zeolitic materials that are not nanosize, for example. For example the nanosize zeolite may have at least 50% higher ratio of surface area to volume compared to zeolitic materials that are not nanosize, optionally at least 100% higher ratio, optionally at least two times higher ratio, optionally at least five times higher ratio, optionally at least ten times higher ratio.

The nanosize zeolite may be supported, or added, by any method(s) known to one skilled in the art. In an embodiment, these methods may include incipient wetness impregnation. In an alternative embodiment, the nanosize zeolite may be admixed with a support material. In a further embodiment, the nanosize zeolite may be supported in-situ with the support material or extruded. In an additional embodiment, the nanosize zeolite may be supported by spray-coating it onto a support material. It is further contemplated that such support processes may include layering the nanosize zeolite onto the support material, such as the support materials described below or optionally polymer spheres, such as polystyrene spheres, for example. It is even further contemplated that such support processes may include the utilization of zeolitic membranes, for example.

In one specific embodiment, the nanosize zeolite is supported by a support material and the nanosize zeolite is added to the support material via incipient wetness impregnation. In an embodiment, this process includes dispersing a nanosize zeolite in a diluent, such as non-limiting examples of methanol or toluene, to yield individually dispersed crystals, or individually dispersed nanoparticles. A support material may then be added to the solution and mixed until dry. In an embodiment, the dispersing of the nanoparticles of the nanosize zeolite in a solution is naturally dispersed or may be aided by agitation. Any suitable means of agitation may be used. In a specific embodiment, the agitation includes sonication.

In the incipient wetness impregnation method, the nanoparticles may have an affinity for one another and may form agglomerations inside the pores of the substrate. These agglomerations may become bound inside the support material, causing the nanosize zeolite to be supported by the support material. But agglomerations of the nanoparticles within the pores of the substrate are not necessary for the nanoparticles to be supported by the substrate.

In another embodiment, the nanoparticles may be added to the support aided by the use of carriers. In an embodiment, this process includes dispersing a nanosize zeolite in a diluent, such as methanol or toluene, to yield individually dispersed crystals, or individually dispersed nanoparticles. A support material may then be added to the solution and mixed. A carrier may be added to the solution at any point during the mixing. In an embodiment, the carrier is added to the diluent before the nanosize zeolite is added. In another embodiment, the carrier is added to the diluent after the nanosize zeolite is added and before the support material is added. In a further embodiment, the carrier is added after the nanosize zeolite and support material are added to the diluent. In an aspect, the zeolitic material, the catalytically active promoter, the support material or combinations thereof may optionally be contacted with a carrier prior to contact of the zeolitic material with the catalytically active promoter. This may be done by having an ion exchange, or other process of addition, performed after a supporting step.

The carrier may be adapted to aid in the incorporation of the catalytically active promoter into the zeolitic material, for example. In one or more embodiments, the carrier is a nano-sized carrier, or nanocarrier (with the nano-sized carrier defined as for nanosize zeolites, as described above). In an embodiment, the carrier may include aluminum. In a more specific embodiment, the aluminum-containing carrier includes boehmite alumina. In an embodiment, the nanocarrier comprises material that may attract nanoparticles with columbic interaction.

In one embodiment, the nanosize zeolite may be formed by utilizing a carrier to transport the nanosize zeolite into pores of the support material. In an embodiment, the carrier includes boehmite alumina. The carrier may be then be added to a solution containing toluene or methanol. Boehmite alumina is a nano-sized crystallite having particle sizes from about 10 to 15 nm. These nanoparticles have a high surface charge that may adhere small particles, such as nano-zeolites, which may be beneficial in transporting the zeolites into the pores of the silica support material. The formed zeolite may then be dried and subjected to thermal treatment. During thermal treatment, the silica and alumina may bond and hold the zeolite in a cage-like assembly for catalytic activity. In a further embodiment, the carrier may be mixed with a solvent prior to contact with the nanosize zeolite.

In an embodiment, the nanosize zeolite is supported by physical addition of the nanosize zeolite with the zeolitic support. In another embodiment, the nanosize zeolite is supported by forming an extrudable material utilizing a support material in combination with the nanosize zeolite to form extrudates and/or tablets.

The nanosize zeolite may be chemically modified so that it will graft onto a support. In an embodiment, the nanosize zeolite is supported by surface modification of the nanosize zeolite followed by grafting the modified nanosize zeolite onto a support. In an embodiment, the support is selected from the group of silica, alumina, a monolith structure and combinations thereof. In another embodiment, the nanosize zeolite is supported by a process including: surface modifying the nanosize zeolites using a grafting molecule such as a silane (silica having functional groups) to yield a surface modified nanosize zeolite, wherein the surface modified nanosize zeolite has terminal reactive functional groups which may help to graft the nanosize zeolite onto a support.

In an embodiment, the nanosize zeolite is deposited on a support by any suitable means, such as by non-limiting example one selected from the group of dip-coating, spray-coating, and wash-coating and any combinations thereof. The nanosize zeolite may be wash-coated on a monolith or an inert structured support for example.

The nanosize zeolite may be supported in situ with the support material. In an embodiment, the nanosize zeolite particles are created in situ with the support material. In another embodiment, the nanosize zeolite particles are simultaneously created and supported in situ with the support material.

The catalysts described herein may increase the effective diffusivity of the reactants, thereby increasing reactant conversion to desired products. Furthermore, the catalysts may result in processes exhibiting improved product selectivity over processes utilizing conventional zeolitic materials. In addition, activity of such processes may be increased due to an increase of accessibility of active sites, which thereby increases the effective number of active sites per weight of catalyst over larger non-nanosize zeolites.

In one embodiment, a catalytically active element, such as a catalytically active metal, may be incorporated into the nanosize zeolite by, for example, ion-exchange or impregnation of the zeolitic material, or by incorporating the active element in the synthesis materials from which the zeolitic material is prepared. As described herein, the term "incorporated into the zeolitic material" refers to incorporation into the framework of the zeolitic material, incorporation into channels of the zeolitic material (i.e., occluded) or combinations thereof.

The catalytically active element may be in a metallic form, combined with oxygen (e.g., metal oxide) or include derivatives of the compounds described below, for example. Suitable catalytically active metals depend upon the particular process in which the catalyst is intended to be used and generally include, but are not limited to, alkali metals (e.g., Li, Na, K, Rb, Cs, Fr), rare earth "lanthanide" metals (e.g., La, Ce, Pr), Group IVB metals (e.g., Ti, Zr, Hf), Group VB metals (e.g., V, Nb, Ta), Group VIB metals (e.g., Cr, Mo, W), Group IB metals (e.g., Cu, Ag, Au), Group VIIIB metals (e.g., Pd, Pt, Ir, Co, Ni, Rh, Os, Fe, Ru), Group IIIA metals (e.g., Ga), Group IVA metals (e.g., Ge) and combinations thereof, for example. Alternatively (or in combination with the previously discussed metals), the catalytically active element may include a Group IIIA compound (e.g., B), a Group VA compound (e.g., P) or combinations thereof, for example. In one or more embodiments, the catalytically active element is selected from Cs, Na, B, Ga and combinations thereof.

In one or more embodiments, the nanosize zeolite may include less than 15 wt. % sodium of the total weight of active catalyst, optionally less than 10 wt. % sodium, optionally less than 7 wt. % sodium. In one or more embodiments, the nanosize zeolite may include less than 25 wt. % aluminum of the total weight of active catalyst, optionally less than 20 wt. % aluminum, optionally less than 14 wt. % aluminum. In one or more embodiments, the nanosize zeolite may include at least 10 wt. % cesium of the total weight of active catalyst, optionally at least 20 wt. % cesium, optionally at least 25 wt. % cesium. In one or more embodiments, the nanosize zeolite may include less than 30 wt. % silicon of the total weight of active catalyst, optionally less than 25 wt. % silicon, optionally less than 18 wt. % silicon. In one or more embodiments, the nanosize zeolite may include less than 10 wt. % boron of the total weight of active catalyst, optionally less than 5 wt. % boron, optionally less than 3 wt. % boron. The balance of the nanosize zeolite will generally be formed of oxygen. If other elements are included in the material, then these amounts may be altered.

Acidic Zeolites

In addition to basic or neutral zeolites, acidic zeolites may be used as a catalyst to convert n-butene and a C-1 source to make C5 Di-olefins. Non-limiting examples of acidic zeolites include HY, MOR, SAPO-34, and ZSM-5. Acidic zeolites may be modified, for instance, by modifying the silica to alumina ratio. The silica to alumina ratio may be modified by traditional techniques, such as steaming or steaming followed by leaching. After leaching, Si:Al ratios of the modified acidic zeolite, such as a modified ZSM-5, may range from 80 to 300 or from 100 to 200 or from 120 to 160. Acidic zeolites may also be modified by ion-exchange with a catalytically active metal. In one embodiment, a catalytically active element, such as a catalytically active metal, may be incorporated into the acidic zeolite by, for example, ion-exchange or impregnation of the zeolitic material, or by incorporating the active element in the synthesis materials from which the zeolitic material is prepared. As described herein, the term "incorporated into the zeolitic material" refers to incorporation into the framework of the zeolitic material, incorporation into channels of the zeolitic material (i.e., occluded) or combinations thereof.

The catalytically active element may be in a metallic form, combined with oxygen (e.g., metal oxide) or include derivatives of the compounds described below, for example. Suitable catalytically active metals depend upon the particular process in which the catalyst is intended to be used and generally include, but are not limited to, alkali metals (e.g., Li, Na, K, Rb, Cs, Fr), rare earth "lanthanide" metals (e.g., La, Ce, Pr), Group IVB metals (e.g., Ti, Zr, Hf), Group VB metals (e.g., V, Nb, Ta), Group VIB metals (e.g., Cr, Mo, W), Group IB metals (e.g., Cu, Ag, Au), Group VIIIB metals (e.g., Pd, Pt, Ir, Co, Ni, Rh, Os, Fe, Ru), Group IIIA metals (e.g., Ga), Group IVA metals (e.g., Ge) and combinations thereof, for example. Alternatively (or in combination with the previously discussed metals), the catalytically active element may include a Group IIIA compound (e.g., B), a Group VA compound (e.g., P) or combinations thereof, for example. In one or more embodiments, the catalytically active element is Ag.

Non-Zeolitic Acidic Catalysts

Non-zeolitic acidic catalyst may also be used in certain embodiments as catalyst in the present disclosure. Examples include alumina (such as Catapal-C1 from Sasol), silica aluminate (such as Kaolin), and silica.

Silica Supported Catalysts

In other embodiments of the present disclosure, silica and titania-supported metal catalysts, including, but not limited to, silica and titania-supported metal oxide and silica and titania-supported metal phosphate catalyst may be used. Examples of silica and titania-supported metal oxide catalyst include silica-supported bismuth oxide catalyst (BiOx/$SiO_2$), silica-supported silver oxide catalyst (AgOx/$SiO_2$), and titania-supported tungsten oxide catalyst (WOx/$TiO_2$). Examples of silica and titania-supported phosphate catalysts include aluminum phosphate catalyst ($AlPO_4$), niobium phosphate catalyst ($NbPO_4$).

Reactors

Embodiments of reactors that may be used with the present disclosure may include, by non-limiting examples: fixed bed reactors; fluid bed reactors; and entrained bed reactors. Reactors capable of the elevated temperature and pressure as described herein, and capable of enabling contact of the reactants with the catalyst, may be considered within the scope of the present disclosure. Embodiments of the particular reactor system may be determined based on the particular design conditions and throughput, as by one of ordinary skill in the art, and are not meant to be limiting on the scope of the present disclosure. An example of a suitable reactor may be a fluid bed reactor having catalyst regeneration capabilities. This type of reactor system employing a riser may be modified as needed, for example by insulating or heating the riser if thermal input is needed, or by jacketing the riser with cooling water if thermal dissipation is required. These designs may also be used to replace catalyst while the process is in operation, by withdrawing catalyst from the regeneration vessel from an exit line or adding new catalyst into the system while in operation.

In another aspect, the one or more reactors may include one or more catalyst beds. In the event of multiple beds, an inert material layer may separate each bed. The inert material may comprise any type of inert substance, including quartz. In an embodiment, a reactor includes between 1 and 10 catalyst beds. In a further embodiment, a reactor includes between 2 and 5 catalyst beds. In addition, the C1 source and n-butene may be injected into a catalyst bed, an inert material layer, or both. In a further embodiment, at least a portion of the C1 source is injected into a catalyst bed(s) and at least a portion of the n-butene feed is injected into an inert material layer(s).

In an alternate embodiment, the entire C1 source is injected into a catalyst bed(s) and all of the n-butene feed is injected into an inert material layer(s). In another aspect, at least a portion of the n-butene feed is injected into a catalyst bed(s) and at least a portion the C1 source is injected into an inert material layer(s). In a further aspect, all of the n-butene feed is injected into a catalyst bed(s) and the entire C1 source is injected into an inert material layer(s).

Figure 3:
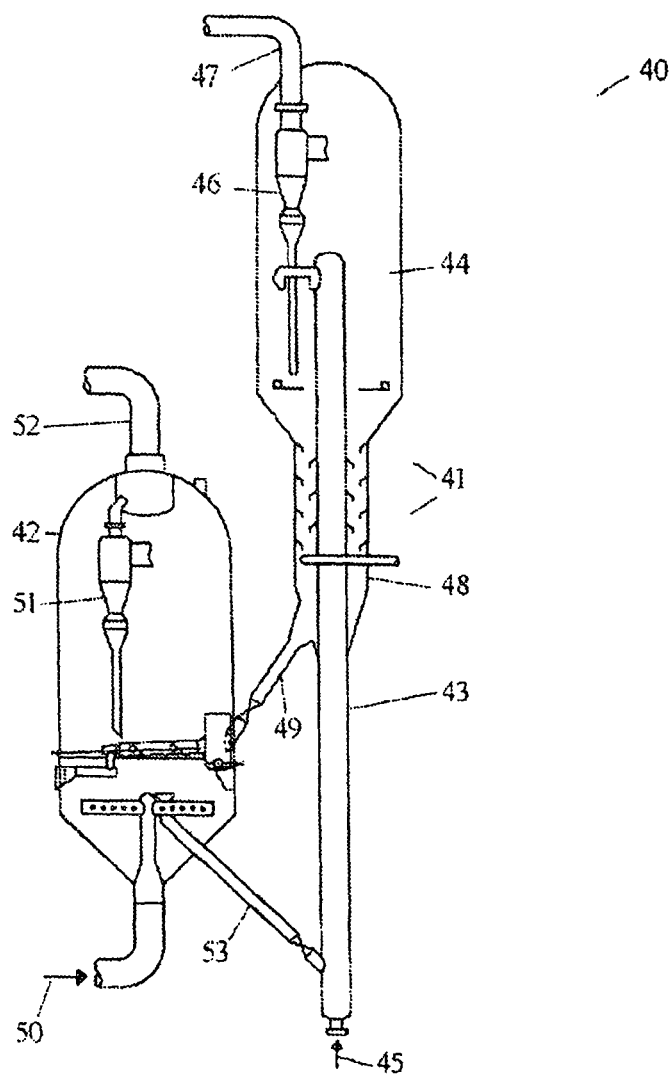
FIG. 3 is a schematic illustration of an embodiment of the present disclosure having the capability for continuous reaction with catalyst regeneration.

An example of a fluidized bed reactor having catalyst regeneration capabilities that may be employed with the present disclosure is illustrated in FIG. 3. This type of reactor system employing a riser may be modified as needed, for example by insulating or heating the riser if thermal input is needed, or by jacketing the riser with cooling water if thermal dissipation is required. These designs may also be used to replace catalyst while the process is in operation, by withdrawing catalyst from the regeneration vessel from an exit line (not shown) or adding new catalyst into the system while in operation. The riser reactor may be replaced with a downer reactor (not shown). In an embodiment (not shown), the reaction zone includes both riser and downer reactors.

FIG. 3 is a schematic illustration of an embodiment of the present disclosure having the capability for continuous reaction with catalyst regeneration. The reactor system (40) generally includes two main zones for reaction (41) and regeneration (42). A reaction zone may have a vertical conduit, or riser (43), as the main reaction site, with the effluent of the conduit emptying into a large volume process vessel, separation vessel (44). In riser (43), feed stream (45), such as n-butene and formaldehyde, may be contacted with a fluidized catalyst, which may be a relatively large fluidized bed of catalyst, at reactor conditions. The residence time of catalyst and hydrocarbons in riser (43) needed for substantial completion of the reaction may vary as needed for the specific reactor design and throughput design. The flowing vapor/catalyst stream leaving riser (43) may pass from the riser to a solids-vapor separation device, such as a cyclone (46), normally located within and at the top of separation vessel (44). The products of the reaction may be separated from the portion of catalyst that is carried by the vapor stream by means of one or more cyclone separators (46) and the products may exit cyclone separators (46) and separation vessel (44) via exit line (47). The spent catalyst falls downward to stripper (48) located in a lower part of separation vessel (44). Catalyst may be transferred to a regeneration vessel (42) by way of a conduit (49) connected to the stripper (48).

The catalyst may be continuously circulated from reaction zone (41) to regeneration zone (42) and then again to reaction zone (41). The catalyst may therefore act as a vehicle for the transfer of heat from zone to zone as well as providing the necessary catalytic activity. Catalyst from reaction zone (41) that is being transferred to regeneration zone (42) may be referred to as "spent catalyst". The term "spent catalyst" is not intended to be indicative of a total lack of catalytic activity by the catalyst particles. Catalyst, which is being withdrawn from regeneration zone (42), is referred to as "regenerated" catalyst. The catalyst may be regenerated in regeneration zone (42) by heat and contact with regeneration stream (50). Regeneration stream (50) may include oxygen and/or include steam. The regenerated catalyst may be separated from the regeneration stream by the use of one or more cyclone separators (51) that may enable the removal of the regeneration vessel (42) via line (52). The regenerated catalyst may be transferred via line (53) to the lower section of riser (43) where it is in contact with feed stream (45) and may flow up riser (43).

The n-butene and C1 source coupling reaction may have a n-butene conversion percent greater than 0.01 mol %. In an embodiment the n-butene and C1 source coupling reaction is capable of having a n-butene conversion percent in the range of from 0.05 mol % to 40 mol %. In a further embodiment the n-butene and C1 source coupling reaction is capable of having a n-butene conversion in the range of from 2 mol % to 40 mol %, optionally from 5 mol % to 35 mol %, optionally from 20 mol % to 30 mol %.

In an aspect the n-butene and C1 source coupling reaction is capable of selectivity to piperylene greater than 1 mol %, relative to n-butene. In another aspect, the n-butene and C1 source coupling reaction is capable of selectivity to piperylene in the range of from 1 mol % to 99 mol %.

EXAMPLES

Example 1

The catalyst FAU (Cs, Na/X-type, basic, EXT-272) was evaluated for formaldehyde addition with C4-olefin (2-butene) to produce a C5 di-olefin. The catalysts (12 mL) were crushed and sieved to a 60/40 mesh size and were packed in a ceramic lined SS reactor (0.5 inch i.d.) with a top flow of reagents. The catalysts were pretreated in a flow of nitrogen overnight at 520° C. for 2 h and cooled to reaction temperature 420° C., reactor pressure 1 psig. The feed composition was 10% vol 2-butene and balance helium was fed to the reactor. Pure and anhydrous formaldehyde (C1-source) was produced by de-polymerization of trioxane.

The basic zeolite catalyst (EXT-272, Cs-B/X) showed reaction (C4=conversion about 9%) to form a product stream containing 2-methyl butene-1, N-pentane, Iso-pentane, t-2 pentene, c-2-pentene, 2-methyl butene 2, t-1,3 pentadiene and C-1,3 pentadiene. 1,3 pentadiene was identified as the major product.

Example 2

1-butene and formaldehyde on $AlPO_4$ catalyst were reacted at 375° C., at a pressure of 1 bar, a C4:C1 ratio of 6.3:1, and a WHSV=~3 g/gcat/h. The feed was approximately 30 vol. % pure 1-butene and 5 vol. % formaldehyde (from trioxane decomposition), balanced in $N_2$ with total flow rate of 200 ml/min (STP). The catalyst was prepared as indicated in Ivanova I., et al., Appl Cat A, 2012, 441, 21. Synthesis of isoprene from formaldehyde and isobutene over phosphate catalysts, which is incorporated herein by reference.

Results are shown in Table 1

TABLE 1

| Conversion (%) 1-butene | Selectivity (%) | | | | | |
|---|---|---|---|---|---|---|
| | Cracking | Isomerization | Pentanes | Pentenes | Isoprene | PIPs |
| 60 | 1 | 96 | 0.3 | 0.2 | 0.4 | 1.8 |

Example 3

2-butene and formaldehyde on $AlPO_4$ catalyst were reacted under the same conditions as described in Example 2. Results are shown in Table 2

TABLE 2

| Conversion (%) 2-butene | Selectivity (%) | | | | | |
|---|---|---|---|---|---|---|
| | Cracking | Isomerization | Pentanes | Pentenes | Isoprene | PIPs |
| 15 | 1 | 91 | 2 | 0.5 | 3.5 | 2 |

With respect to Examples 2 and 3, the majority of the selectivity (over 90%) is to isomerization of the feed n-butene, which includes double bond shift products and isobutylene. While C4 to C5 conversion is less than 2%, the selectivity to C5 dienes is more than 50% relative to formaldehyde.

Example 4

Different ZSM-5 catalysts were evaluated with 1-butene and formaldehyde using the reaction conditions as in Example 2. The results are shown in table 5.

TABLE 5

| Catalyst | C4 to C5 Conversion (%) | Selectivity (%) | | | |
|---|---|---|---|---|---|
| | | Pentanes | Pentenes | Isoprene | PIPs |
| ZSM-5 (Si/Al = 15) | 3 | 66 | 5 | 6 | 23 |
| ZSM-5 (Si/Al = 140) | 3 | 71 | 2 | 3 | 24 |
| Ag/ZSM-5 (Si/Al = 15) | 21 | 16 | 31 | 45 | 7 |

By changing the Si/Al ratio, the C4 to C5 conversions and selectivity to C5 dienes remain almost the same. By ion-exchange of silver on ZSM-5, the C4 to C5 conversion increased to 21%. Without being bound by theory, it is believed that this conversion cannot be achieved solely from the reaction of C4 plus formaldehyde, i.e., the C4 conversion should only reach ~16% with 100% conversion of formaldehyde. This result suggests that some of the C4 to C5 conversion is not from the reaction of C4 with formaldehyde but due to another reaction scheme. The selectivity to C5 dienes increases to about 50%, with the rest of the products being pentanes and pentenes. Besides the C4 to C5 conversion, there is also a significant amount of C4 converted to C3 (~15%) and C6+(50%) over Ag/ZSM-5 catalyst.

Example 5

A silica-aluminate catalyst, Kaolin, was evaluated with 1-butene and formaldehyde using the reaction conditions as in Example 2. The results are shown in table 6.

| C4 to C5 Conversion (%) | Selectivity (%) | | | |
|---|---|---|---|---|
| | Pentanes | Pentenes | Isoprene | PIPs |
| 3 | 0 | 5 | 50 | 45 |

The term "conversion" unless indicated otherwise refers to the molar percentage of reactant (e.g. n-butene) that undergoes a chemical reaction.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

The term "regenerated catalyst" refers to a catalyst that has regained enough activity to be efficient in a specified process. Such efficiency is determined by individual process parameters.

The term "spent catalyst" refers to a catalyst that has lost enough catalyst activity to no longer be efficient in a specified process. Such efficiency is determined by individual process parameters.

The term "zeolite" refers to a molecular sieve containing an aluminosilicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves. An X-zeolite is defined as having a Si/Al molar ratio between 1.0 and 2.0. A Y-zeolite is defined as having a Si/Al molar ratio greater than 2.0.

Depending on the context, all references herein to the "disclosure" may in some cases refer to certain specific embodiments only. In other cases it may refer to subject matter recited in one or more, but not necessarily all, of the claims. While the foregoing is directed to embodiments, versions and examples of the present disclosure, which are included to enable a person of ordinary skill in the art to make and use the disclosures when the information in this patent is combined with available information and technology, the disclosures are not limited to only these particular embodiments, versions and examples. Other and further embodiments, versions and examples of the disclosure may be devised without departing from the basic scope thereof and the scope thereof is determined by the claims that follow.

What is claimed is:

1. A process comprising:
   reacting a C-1 source with n-butene to form a C-5 diolefin, wherein, in the step of reacting the C-1 source with n-butene a catalyst is employed, and wherein the catalyst comprises a basic zeolite or a neutral zeolite.

2. The process of claim 1, wherein the C-5 diolefin is 1,3 pentadiene, isoprene, or a combination thereof.

3. The process of claim 1, wherein the n-butene is 1-butente, 2-butene, or a combination thereof.

4. The process of claim 1, wherein the C-1 source is formaldehyde or formalin.

5. The process of claim 1, wherein the basic zeolite or neutral zeolite is a faujisite, X-type or Y-type zeolite.

6. The process of claim 1, wherein the basic zeolite or neutral zeolite is modified by the addition of an occluded metal oxide.

7. The process of claim 6, wherein the occluded metal oxide is cesium oxide or copper oxide.

8. The process of claim 1, wherein the basic zeolite or neutral zeolite is a nano-sized basic or neutral zeolite with a particle size less than 1000 nm.

9. The process of claim 8, wherein the catalyst further comprises a promoter selected from the group consisting of Ru, Rh, Ni, Co, Pd, Pt, Mn, Ti, Zr, V, Nb, K, Cs, Ga, P, B, Rb, Ag, Ge, Cu, Mg, and Na and combinations thereof.

10. The process of claim 8, wherein the catalyst further comprises a support material that is selected from the group consisting of silica, alumina, aluminosilica, titania, and zirconia and combinations thereof.

11. The process of claim 1, wherein the catalyst comprises the basic zeolite.

12. The process of claim 1, wherein the catalyst comprises the neutral zeolite.

13. The process of claim 1, wherein reacting the reacting of the C-1 source with n-butene to form the C-5 diolefin occurs in one or more reactors with one or more catalyst beds.

14. A process comprising:
   reacting a C-1 source with n-butene to form a C-5 diolefin, wherein selectivity to 1,3 pentadienes is greater than 2 mol % relative to the C-1 source.

15. A process comprising:
   reacting a C-1 source with n-butene to form 1,3 pentadiene.

* * * * *